(12) United States Patent
Chevalier et al.

(10) Patent No.: US 7,780,971 B2
(45) Date of Patent: Aug. 24, 2010

(54) COMPOSITION CONTAINING FIBERS, SPHERICAL PARTICLES AND PLATELETS, AND ITS USES

(75) Inventors: Veronique Chevalier, Villecresnes (FR); Albane Agostini, Verrieres le Buisson (FR)

(73) Assignee: L'Oreal, Paris (FR)

(*) Notice: Subject to any disclaimer, the term of this patent is extended or adjusted under 35 U.S.C. 154(b) by 3 days.

(21) Appl. No.: 10/100,907

(22) Filed: Mar. 20, 2002

(65) Prior Publication Data

US 2002/0192250 A1     Dec. 19, 2002

(30) Foreign Application Priority Data

Mar. 20, 2001   (FR) ................................. 01 03767

(51) Int. Cl.
   *A61K 8/02*     (2006.01)
(52) U.S. Cl. ..................... 424/401; 424/489; 424/497; 424/78.03; 514/938
(58) Field of Classification Search ................ 424/401, 424/489, 78.03, 497; 514/844, 938, 936
See application file for complete search history.

(56) References Cited

U.S. PATENT DOCUMENTS

| | | | |
|---|---|---|---|
| 4,659,562 A * | 4/1987 | Arraudeau et al. ............ 424/63 |
| 5,702,519 A * | 12/1997 | Nitta et al. ................... 106/442 |
| 5,965,146 A * | 10/1999 | Franzke et al. ............... 424/401 |
| 6,171,550 B1 * | 1/2001 | Bendiner ....................... 422/28 |
| 6,489,283 B1 * | 12/2002 | Afriat .......................... 510/417 |
| 2003/0170281 A1 * | 9/2003 | Riedel et al. ................. 424/401 |

FOREIGN PATENT DOCUMENTS

| | | | |
|---|---|---|---|
| EP | 0 106 762 A | | 4/1984 |
| EP | 1 053 742 A | | 11/2000 |
| GB | 2002652 | * | 2/1979 |
| JP | 62-238211 | | 10/1987 |
| JP | EP 1 036 553 A2 | * | 3/2000 |
| JP | 2002-047120 | | 2/2002 |

OTHER PUBLICATIONS

Translation of JP 7-196440, published Aug. 1, 1995, Uchibori et al.*
U.S. Appl. No. 10/102,729, filed Mar. 22, 2002, Chevalier, et al.
U.S. Appl. No. 10/102,632, filed Mar. 22, 2002, Chevalier.

* cited by examiner

*Primary Examiner*—Sreeni Padmanabhan
*Assistant Examiner*—Shobha Kantamneni
(74) *Attorney, Agent, or Firm*—Oblon, Spivak, McClelland, Maier & Neustadt, L.L.P.

(57) ABSTRACT

The invention relates to a composition containing an oily phase dispersed in an aqueous phase, fibers, spherical particles and platelets. The composition has very good stability and applies very uniformly to the skin, with no phenomenon of pilling or of aggregation. It may especially constitute and oil-in-water emulsion that may be used as a cosmetic composition. The invention also relates to the use of the said composition especially to care for, treat, make up or cleanse the skin, the lips, the eyelashes and/or the hair.

21 Claims, No Drawings

COMPOSITION CONTAINING FIBERS, SPHERICAL PARTICLES AND PLATELETS, AND ITS USES

BACKGROUND OF THE INVENTION

1. Field of the Invention

The present invention relates to a composition comprising, preferably in a physiologically acceptable medium, an oily phase dispersed in an aqueous phase, fibers, spherical particles and platelets, and to the use of the composition, preferably to care for, treat and/or make up keratin materials such as body or facial skin, the hair, the eyelashes and/or the lips.

2. Discussion of the Background

Document JP 07-196 440 discloses cosmetic compositions containing short polyamide fibers, the compositions allegedly having a velvety feel and good cosmetic staying power. However, the incorporation of the fibers, and in particular of these polyamide fibers, into dispersions comprising an oily phase dispersed in an aqueous phase, and in particular into oil-in-water (O/W) emulsions that are dispersions stabilized with emulsifiers, poses problems when applying the composition to keratin materials such as the skin, and especially when there is a large amount of fibers. Specifically, the fibers, especially when they are in a relatively large amount, have a tendency to aggregate in O/W emulsions containing them. Moreover, these emulsions containing fibers have a tendency to "pill" on the skin, that is to say to be applied in packets appearing as small balls on the skin.

OBJECT OF THE INVENTION

There is thus still a need for O/W dispersions, and especially O/W emulsions, containing fibers, and especially polyamide fibers, even in a large amount, which do not have the drawbacks of the prior art.

SUMMARY OF THE INVENTION

The inventors have discovered, unexpectedly, that combining fibers, spherical particles and platelets makes it possible to avoid the problems of pilling and of aggregation, believed to be caused by the fibers, and to prepare, e.g., oil-in-water emulsions containing fibers, which do not pose any problems when applied to the skin, even in the presence of a large amount of fibers.

DETAILED DESCRIPTION OF THE INVENTION

The present invention relates to a composition comprising, preferably in a physiologically acceptable medium, an oily phase dispersed in an aqueous phase, fibers, spherical particles and platelets.

The expression "physiologically acceptable medium" means herein a medium that is compatible with keratin materials such as the skin, the lips, the scalp, the eyelashes, the eyes and/or the hair.

The dispersion may preferably be an O/W emulsion.

The composition of the invention makes it possible not only to prevent the fibers from aggregating, but also to facilitate the application of the composition containing them to keratin materials, and in particular to the skin. Thus, the composition according to the invention does not "pill" and therefore does not form small balls when applied to the skin. In addition, it disintegrates easily, that is to say that it can be easily applied and is deposited in a sufficient amount and in a uniform manner on the skin or the keratin material on which it is applied. This effect of combining platelets and spherical particles is found for any composition containing fibers, and is especially useful for dispersions.

A subject of the invention is also the cosmetic use the combination of platelets and spherical particles in a cosmetic composition containing fibers, to prevent the fibers from aggregating, to prevent the composition from pilling, and to facilitate the application (and the disintegration) of the composition to keratin materials and especially the skin.

In the present patent application, the expression "spherical particles" means particles having or substantially having the shape of a sphere, which are insoluble in the medium of the composition, even at the melting point of the medium (e.g., about 100° C.).

In addition, the terms "platelets" and "leaflets" mean herein particles of parallelepipedal shape (rectangular or square surface area), discoid shape (circular surface area) or ellipsoid shape (oval surface area), characterized by three dimensions: a length, a width and a height, these particles being insoluble in the medium of the composition according to the invention, even at the melting point of the medium (e.g., about 100° C.).

The composition of the invention may comprise one or more kinds of fiber, one or more kinds of spherical particle, and one or more kinds of platelet.

Fibers

The fibers which may be used in the composition of the invention include hydrophilic or hydrophobic fibers, of natural or synthetic, mineral or organic origin.

These fibers may be short or long, individual or organized, for example braided. They are generally of cylindrical shape, unlike the platelets, which are of parallelepipedal, etc. shape, or the spherical particles, which are of spherical shape. They may have any morphology and in particular may have a circular or polygonal (square, triangular, hexagonal or octagonal) cross section depending on the specific application envisaged. In particular, their ends may be blunted and/or polished to prevent injury.

The fibers may have a length (L) ranging from 1 μm (0.001 mm) to 10 mm, preferably from 0.1 μm to 5 mm and better still from 0.1 mm to 1.5 mm. Their cross section may be within a circle of diameter (D) ranging from 1 nm (0.001 μm) to 100 μm, preferably ranging from 1 nm (0.001 μm) to 50 μm and better still from 5 μm to 40 μm.

Preferably, the fibers used according to the present invention have a shape factor, i.e. a ratio L/D (length/diameter) ranging from 3.5 to 2,500, better still from 5 to 500 and even better still from 5 to 150.

The yarn count of fibers is often given in denier or decitex. The denier is the weight in grams for 9 km of yarn. The fibers used according to the invention preferably have a yarn count ranging from 0.15 to 30 denier and better still from 0.18 to 18 denier.

The shape factor, the yarn count and the morphology of the fibers are the three factors that are important for defining a fiber.

The fibers may be those used in the manufacture of textiles and in particular silk, cotton, wool or flax fibers, cellulose fibers extracted in particular from wood, plants or algae, polyamide (Nylon®) fibers, modified cellulose (rayon, viscose or acetate, in particular rayon acetate) fibers, poly-p-phenyleneterephthalamide fibers, in particular Kevlar® fibers, acrylic fibers, in particular polymethyl methacrylate or poly(2-hydroxyethyl methacrylate) fibers, polyolefin fibers and in particular polyethylene or polypropylene fibers, glass, silica or aramid fibers, carbon fibers, in particular in the form of graphite, Teflon fibers, insoluble collagen fibers, polyester, polyvinyl chloride, polyvinylidene chloride, polyvinyl alcohol, polyacrylonitrile, chitosan, polyurethane or polyethylene phthalate fibers, and fibers formed from a mixture of polymers such as those mentioned above, for instance polyamide/polyester fibers.

Examples of polyurethane fibers include poly(urethane-urea) polymer fibers, belonging to the elastane class, and especially those sold under the name Lycrag by the company DuPont.

Resorbable synthetic fibers used in surgery may also be used, for instance the fibers prepared from glycolic acid and from caprolactone (Monocryl from the company Johnson & Johnson); resorbable synthetic fibers such as the copolymer of lactic acid and of glycolic acid (Vicryl from the company Johnson & Johnson); terephthalic polyester fibers (Ethibond from the company Johnson & Johnson) and stainless steel yams (Acier from the company Johnson & Johnson).

Mixtures of fibers may also be used.

Moreover, the fibers may or may not be surface-treated and may be coated or uncoated. They may especially be coated and/or functionalized fibers, the term "functionalized" meaning that the fibers are surface-treated so as to modify their properties.

Coated fibers which may be used in the invention include polyamide fibers coated with copper sulphide for an antistatic effect (for example R-STAT from the company Rhodia) or another polymer allowing a particular organization of the fibers (specific surface treatment) or a surface treatment which induces colour/hologram effects (for example Lurex fiber from the company Sildorex).

The fibers can also be functionalized, that is to say be modified so as to have a specific function. This functionalization of the fibers can be carried out both on the fibers and in the fibers and by any method which makes it possible to attach a compound to the fibers or to trap it within the cavities formed by the geometry of the fibers. Mention may be made, as methods, of, for example, coating the fibers with an active principle; fixing, to the fibers, particles enclosing an active principle, such as nanocapsules or nanospheres; adsorption in the fibers; or fixing by chemical reaction. It is thus possible to use fibers having specific functional purposes, for example fibers which are stabilized against UV radiation by modification with chemical or physical sunscreens; fibers which have been rendered bactericidal or antiseptic by modification with preservatives or antibacterials; fibers which have been coloured by modification with colouring molecules; fibers which have been rendered keratolytic or desquamating by modification with keratolytic or desquamating agents; fibers which have been rendered hydrating by modification with hydrating agents or water-retaining polymers; fibers which have been rendered fragrant by modification with a fragrance; fibers which have been rendered analgesic or soothing by modification with an antiinflammatory or a soothing agent; or fibers which have been rendered resistant to perspiration by modification with an antiperspirant.

According to their properties, the fibers used according to the present invention may be introduced into an aqueous medium, an oily medium or into a powder.

The fibers which may be used according to the invention are preferably chosen from polyamide fibers, poly-p-phenyleneterephthalamide fibers and cotton fibers, and mixtures thereof. Their length may preferably range from 0.1 to 10 mm and preferably from 0.1 to 1 mm, their mean diameter may range from 5 to 50 µm and the shape factor preferably ranges from 5 to 150.

In particular, the polyamide fibers sold by Etablissements P. Bonte under the name Polyamide 0.9 dtex 0.3 mm, having a mean diameter of from 15 to 20 µm, a yarn count of about 0.9 dtex (0.81 denier) and a length ranging from 0.3 mm to 1.5 mm, may be used. Poly-p-phenyleneterephthalamide fibers with a mean diameter of 12 µm and a length of about 1.5 mm may also be used, such as those sold under the name Kevlar Floc by the company Du Pont Fibers. These polyamide fibers are preferably introduced into an oily medium or introduced via a dry route into a powder.

Cotton fibers with a mean diameter of 20 µm, a length of 0.3 mm and a shape factor of 15 may also be used, such as those sold by the company Filature de Lomme, by the company Textiles des Dunes, by the Institut Textile de France or by the company Velifil.

The fibers may be present in the composition according to the invention in an amount ranging, for example, from 0.1% to 50% by weight, preferably from 0.5% to 30% by weight, better still from 1% to 20% by weight and even better from 2% to 15% by weight relative to the total weight of the composition, including 4, 5, 7, 9, 10, 12 and 14%.

Spherical Particles

The spherical particles according to the invention have or substantially have the shape of a sphere and may be hollow or solid. Advantageously, the particles of the invention have a particle size (number-average diameter) ranging from 0.1 µm to 250 µm, better still from 1 µm to 150 µm and even better from 10 µm to 100 µm, including 20, 30, 40, 50, 60, 70, 80 and 90 µm.

Useful spherical particles include organic and mineral microspheres. As non-limiting examples of spherical particles that may be used in the composition of the invention, mention may be made, for example, of silica powder; polyamide particles and especially Nylon 12, for instance the product sold under the name Orgasol by the company Atochem; polyethylene powders; microspheres based on acrylic copolymers, such as those made of ethylene glycol dimethacrylate/lauryl methacrylate copolymer sold by the company Dow Corning under the name Polytrap; expanded powders such as hollow microspheres, and especially the microspheres sold under the name Expancel by the company Kemanord Plast or under the name Micropearl F 80 ED by the company Matsumoto; powders of natural organic materials such as corn starch, wheat starch or rice starch, that may or may not be crosslinked, such as the starch powders crosslinked with octenylsuccinate anhydride, sold under the name Dry-Flo by the company National Starch; silicone resin microbeads such as those sold under the name Tospearl by the company Toshiba Silicone; and mixtures thereof.

The spherical particles of the invention may be present in amounts ranging, for example, from 0.1% to 30% by weight, preferably from 0.5% to 25% by weight and better still from 1% to 10% by weight relative to the total weight of the composition, including 2, 4, 6 and 8%.

Platelets

As mentioned above, the platelets are particles of parallelepipedal shape (rectangular or square surface area), discoid shape (circular surface area) or ellipsoid shape (oval surface area), characterized by three dimensions: a length, a width and a height. When the shape is circular, the length and width are identical and correspond to the diameter of a disc, whereas the height corresponds to the thickness of the disc. When the surface area is oval, the length and width correspond, respectively, to the major axis and the minor axis of an ellipse and the height corresponds to the thickness of the elliptical disc formed by the platelet. When it is a parallelepiped, the length and width may be of identical or different sizes: when they are of the same size, the shape of the surface area of the parallelepiped is square; in the contrary case, the shape is rectangular. As regards the height, it corresponds to the thickness of the parallelepiped.

The length of the platelets used according to the invention preferably ranges from 0.01 to 100 µm, better still from 0.1 to 50 µm and even better from 1 to 50 µm, including 10, 20, 30 and 40 µm. The width of these platelets preferably ranges from 0.01 to 100 µm, better still from 0.1 to 50 µm and even better from 1 to 10 µm, including 3, 4, 6 and 8 µm. The height (thickness) of these platelets preferably ranges from 0.1 nm to 1 µm (0.1 to 1,000 nm), better still from 1 nm to 600 nm and even better from 1 nm to 500 nm, including 25, 50, 100, 200, 300, and 400 nm.

Examples of platelets that may be used in the composition of the invention include mineral and organic pigments, lamellar silicates, and mixtures thereof The term "pigments" should be understood as meaning white or coloured, mineral or organic particles, which are insoluble in the medium of the composition, and which are intended to colour and/or opacify the composition.

Mineral pigments that may be used in the invention include titanium oxide, zirconium oxide or cerium oxide, and also zinc oxide, iron oxide or chromium oxide, and ferric blue, and mixtures thereof. Organic pigments that may be used in the invention include carbon black and barium, strontium, calcium and aluminium lakes, and mixtures thereof.

Lamellar silicates include clays, talcs, micas and nacres, and mixtures thereof.

The clays are mixed silicates of natural or synthetic origin containing several (two or more) types of cation chosen from alkali metals (for example Na, Li or K) or alkaline-earth metals (for example Be, Mg or Ca), transition metals and aluminium.

Clays that may be used in the invention include, for example, sodium magnesium silicate, clays of the kaolin family, such as kaolin or kaolinite, dickite and nacrite; clays of the halloysite, dombassite, antigorite, benthierine or pyrophyllite family; montmorillonites; beidellite; vermiculites; stevensite; hectorites; saponites; chlorites; sepiolite; smectite, and also these clays chemically modified, for example, with acrylic acids, polysaccharides (for example carboxymethylcellulose) or organic cations, and mixtures thereof.

The talcs are hydrated magnesium silicates usually comprising aluminium silicate. The crystal structure of talc consists of repeated layers of a sandwich of brucite between layers of silica.

The micas are aluminium silicates optionally comprising iron and/or alkali metals. They have the property of being able to divide into thin layers (about 1 µm). They generally range in size from 5 to 150 µm, preferably from 10 to 100 µm and better still from 10 to 60 µm for the largest size (length), and a height (thickness) of from 0.1 to 0.5 µm. The micas include phlogopite, muscovite, fluorophlogopite and vermiculite, and mixtures thereof. Mention may also be made of micaceous clays such as illite.

The "nacres" should be understood as meaning iridescent particles, produced especially by certain molluscs in their shell or else synthesized, which serve to modify the texture of the composition and also the matt/gloss effect. Nacres are generally micas that are surface-treated to obtain this iridescent effect. Nacres that may be used in the invention include, for example, micas coated with titanium oxide, with iron oxide, with natural pigment and/or with bismuth oxychloride, such as coloured or uncoloured titanium oxide-mica (or titanium-mica), and mixtures thereof.

According to one particularly preferred embodiment of the present invention, the platelets are chosen from sodium magnesium silicate; kaolin and kaolinite; montmorillonites; hectorites; talcs; micas; nacres, and mixtures thereof. Advantageously, the platelet used more particularly in the composition of the invention is kaolin, such as the product sold under the name Coslin C-100 by the company Engelhard; talc, such as those sold under the names Rose Talc and Talc SG-2000 by the company Nippon Talc; mica, such as those sold under the names Mica M RP and Silk Mica by the company Merck; titanium micas, such as mica-titanium oxide-brown iron oxide (CTFA: Mica/Iron oxides/Titanium oxide) sold under the name Cloisonne Rouge Flambe 440 X by the company Engelhard; or a modified hectorite such as, for example, a bentone and more particularly the mixture "cyclomethicone, Quaternium-18-hectorite, SD alcohol 40" (85/10/5) (CTFA name) sold under the name Bentone Gel VS-5 by the company Rheox.

The amount of platelets may range, for example, from 0.1% to 30% by weight, preferably from 0.25% to 25% by weight and better still from 0.5% to 10% by weight relative to the total weight of the composition, including 1, 3, 5, 7 and 9%.

Oily Phase

The oily phase of the composition according to the invention is not limited, and may generally represent from 10% to 50% by weight and preferably from 15% to 30% by weight relative to the total weight of the composition.

The oily phase usually contains at least one oil. Examples of oils that may be used in the composition of the invention include:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglyceride or alternatively, for example, sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides for instance those sold by the company Stearineries Dubois or those sold under the names Miglyol 810, 812 and 818 by the company Dynamit Nobel, jojoba oil or karite butter oil;

synthetic esters and synthetic ethers, especially of fatty acids, for instance oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, and hydrogenated polyisobutene such as Parleam® oil;

fatty alcohols containing from 8 to 26 carbon atoms, for instance cetyl alcohol, stearyl alcohol and a mixture thereof (cetylstearyl alcohol), octyldodesanol, 2-butyloctanol, 2-hexyldecanol, 2-undecylpentadecanol, oleyl alcohol or linoleyl alcohol; -alkoylated and especially ethoxylated fatty alcohols such as oleth-12;

partially hydrocarbon-based and/or silicone-based fluoro oils, for instance those described in document JP-A-2 295 912. Examples of fluoro oils which may also be mentioned include perfluoromethylcyclopentane and perfluoro-1,3-dimethylcyslohexane, sold under the names "Flutes PC1®" and "Flutes PC3®" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the company 3M, or alternatively bromoperfluorooctyl sold under the name "Foralkyl®" by the company Atochem; nonafluoromethoxybutane sold under the name "MSX 451 8®" by the company 3M and nonafluoroethoxyisobutane; perfluoromorpholine derivatives, such as the 4-trifluoromethylperfluoromorpholine sold under the name "PF 5052®" by the company 3M; -silicone oils, for instance volatile or non-volatile polymethylsiloxanes (PDMSs) containing a linear or cyclic silicone chain, that are liquid or pasty at room temperature, especially cyclopolydimethylsiloxanes (cyclomethicones) such as cyclohexasiloxane; polydimethylsiloxanes comprising alkyl, alkoxy or phenyl groups, that are pendent or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyldiphenyltrisiloxanes, 2-phenylethyltrimethylsiloxysilicates and polymethylphenylsiloxanes;

mixtures thereof.

In the list of oils mentioned above, the expression "hydrocarbon-based oil" means any oil mainly comprising carbon and hydrogen atoms, and optionally ester, ether, fluoro, carboxylic acid and/or alcohol groups.

Other fatty substances that may be present in the oily phase. For example, fatty acids containing from 8 to 30 carbon atoms, for instance stearic acid, lauric acid, palmitic acid and oleic acid; waxes, for instance lanolin, beeswax, carnauba wax or candelilla wax, paraffin wax, lignite wax or microcrystalline waxes, ceresin or ozokerite, synthetic waxes such as polyethylene waxes, Fischer-Tropsch waxes; gums such as silicone gums (dimethiconol); silicone resins such as trifluoromethyl-C1-4-alkyldimethicone and trifluoropropyldimethicone; and silicone elastomers, for instance the products sold under the names "KSG" by the company Shin-Etsu, under the names "Trefil", "BY29" or "EPSX" by the company Dow Corning or under the names "Gransil" by the company Grant Industries.

These fatty substances may be chosen in a varied manner by a person skilled in the art so as to prepare a composition having the desired properties, for example in terms of consistency or texture, in view of this disclosure.

Aqueous Phase

The aqueous phase of the composition of the invention generally constitutes from 30% to 85% and preferably from 60% to 75% by weight relative to the total weight of the composition, including 65 and 70%. Water is usually the main component of the aqueous phase, the aqueous phase possibly containing other aqueous soluble components, etc.

Additives

The composition according to the invention may especially constitute an oil-in-water emulsion. In this case, it preferably contains at least one emulsifier chosen from those conventionally used for the preparation of O/W emulsions.

Useful emulsifiers include nonionic surfactants, and especially esters of polyols and of fatty acids containing a saturated or unsaturated chain containing, for example, from 8 to 24 carbon atoms and better still from 12 to 22 carbon atoms, and oxyalkylenated derivatives thereof, that is to say derivatives comprising oxyethylene and/or oxypropylene units, such as glyceryl esters of $C_8$-$C_{24}$ fatty acids, and oxyalkylenated derivatives thereof; polyethylene glycol esters of $C_8$-$C_{24}$ fatty acids, and oxyalkylenated derivatives thereof; sorbitol esters of $C_8$-$C_{24}$ fatty acids, and oxyalkylenated derivatives thereof, sugar (sucrose, glucose or alkylglucose) esters of $C_8$-$C_{24}$ fatty acids, and oxyalkylenated derivatives thereof; and mixtures thereof.

Glyceryl esters of fatty acids that may especially be mentioned include glyceryl stearate (glyceryl mono-, di- and/or tristearate) or glyceryl ricinoleate, and mixtures thereof.

Polyethylene glycol esters of fatty acids that may especially be mentioned include polyethylene glycol stearate (polyethylene glycol mono-, di- and/or tristearate), and more especially polyethylene glycol 50 EO monostearate (CTFA name: PEG-50 stearate), and mixtures thereof.

Fatty acid esters of glucose or of alkylglucose that may be mentioned in particular include glucose palmitate, alkyl glycose sesquistearates, for instance methylglucose sesquistearate, alkylglucose palmitates, for instance methylglucose palmitate or ethylglucose palmitate, methylglucoside fatty esters and more especially the diester of methylglucoside and of oleic acid (CTFA name: methyl glucose dioleate); the mixed ester of methylglucoside and of the oleic acid/hydroxystearic acid mixture (CTFA name: methyl glucose dioleate/hydroxystearate); the ester of methylglucoside and of isostearic acid (CTFA name: methyl glucose isostearate); the ester of methylglucoside and of lauric acid (CTFA name: methyl glucose laurate); the mixture of methylglucoside monoester and diester of isostearic acid (CTFA name: methyl glucose sesqui-isostearate); the mixture of methylglucoside monoester and diester and of stearic acid (CTFA name: methyl glucose sesquistearate) and in particular the product sold under the name Glucate SS by the company Amerchol, and mixtures thereof.

Useful oxyethylenated ethers of fatty acid and of glucose or of alkylglucose include oxyethylenated ethers of fatty acids and of methylglucose, and in particular the polyethylene glycol ether of the diester of methylglucose and of stearic acid containing about 20 mol of ethylene oxide (CTFA name: PEG-20 methyl glucose distearate), such as the product sold under the name Glucam E-20 distearate by the company Amerchol; the polyethylene glycol ether of the mixture of methyl glucose monoester and diester and of stearic acid containing about 20 mol of ethylene oxide (CTFA name: PEG-20 methyl glucose sesquistearate) and in particular the product sold under the name Glucamate SSE-20 by the company Amerchol and the product sold under the name Grillocose PSE-20 by the company Goldschmidt, and mixtures thereof.

Useful sucrose esters include sucrose palmitostearate, sucrose stearate and sucrose monolaurate.

Depending on their nature, these emulsifiers are introduced into the aqueous phase or into the oily phase. There may also be an emulsifier in the aqueous phase and another emulsifier in the oily phase. Such is within the skill of the ordinary artisan in view of this disclosure.

According to one particular embodiment of the invention, the emulsifier(s) is (are) chosen from nonionic surfactants, and especially polyol esters of fatty acids and oxyethylenated derivatives thereof, and more particularly glucose or alkylglucose esters of fatty acids and oxyethylenated derivatives thereof, and mixtures thereof.

The amount of emulsifiers may range, for example, from 0.1% to 15% by weight, preferably from 0.5% to 10% by weight and better still from 1% to 8% by weight relative to the total weight of the composition.

The compositions of the invention may contain adjuvants that are common in the fields under consideration, such as hydrophilic or lipophilic active agents, preserving agents, gelling agents, antioxidants, fragrances, solvents, screening agents, soluble dyes, basic or acidic agents and also lipid vesicles. These adjuvants can be used in the usual proportions, for example in the field of cosmetics, and, for example, from 0.01% to 30% of the total weight of the emulsion, and, depending on their nature, they are introduced into the aqueous phase or into the oily phase of the emulsion, or alternatively into vesicles. These adjuvants and their concentrations should be such that they do not modify the desired property for the emulsion of the invention, all of which is within the skill of the ordinary artisan in view of this disclosure.

Useful active agents include moisturizers such as polyols, for instance glycerol and sorbitol; keratolytic agents; depigmenting agents; slimming agents and any active agent that is suitable for the final aim of the composition.

Depending on the desired fluidity of the composition, one or more hydrophilic or lipophilic gelling agents may be added thereto. Examples of hydrophilic gelling agents include carboxyvinyl polymers, such as carbomers; polyacrylamides and polymers and copolymers of 2-acrylamido-2-methylpropanesulphonic acid, that are optionally crosslinked and/or neutralized, for instance poly(2-acrylamido-2-methylpropane sulphonic acid) sold by the company Hoechst under the trade name "Hostacerin AMPS" (CTFA name: ammonium polyacryldimethyltauramide).

Useful lipophilic gelling agents include modified clays such as bentones, such as the mixture "cyclomethicone, Quaternium-18 hectorite, SD alcohol 40" (10/85/5) (CTFA name) sold under the name Bentone Gel VS-5 by the company Rheox; crosslinked elastomeric organopolysiloxanes such as those sold under the names KSG6 from Shin-Etsu, Trefil E-505C or Trefil E-506C from Dow Corning, Gransil from Grant Industries (SR-CYC, SR DMF10 or SR-DC556), or those sold in the form of gels: KSG15, KSG17, KSG16 and KSG18 from Shin-Etsu, Gransil SR 5CYC gel, Gransil SR DMF 10 gel, Gransil SR DC 556 gel and SF 1204 and JK 113 from General Electric.

When they are present, these gelling agents may generally be used at concentrations ranging from 0.1% to 7% and preferably from 0.1% to 5% by weight of active material relative to the total weight of the composition.

The compositions that are the subject of the invention find their application in a large number of treatments, especially cosmetic or dermatological treatments, and they may thus constitute a cosmetic composition, especially for treating, protecting, caring for, removing make-up from and/or cleansing the skin, the lips and/or the hair, and/or for making up the skin of the lips, the eyelashes and the body.

The compositions according to the invention may be used, for example, as care, make-up-removing and/or cleansing products for the face in the form of creams or milks, or as make-up products (for the skin, eyelashes and lips) by incorporation of pigments or colorants, for example as foundations.

Thus, a subject of the invention is the cosmetic use of the composition as defined above for treating, protecting, caring for, removing make-up from and/or cleansing the skin, the lips and/or the hair, and/or for making up the skin, the lips, the eyelashes and/or the body.

A subject of the invention is also a cosmetic process for treating the skin, including the scalp, the hair, the eyelashes and/or the lips, characterized in that a composition as defined above is applied to the skin, the hair, the eyelashes and/or the lips.

The examples which follow will make it possible to understand the invention more clearly, without, however, being limiting in nature. The amounts indicated are in percentages by weight, except where otherwise mentioned.

The example according to the invention was compared in a test on a panel of 12 users with an identical composition but not containing either the platelets (comparative example 1), or the spherical particles (comparative example 2). The application was performed comparatively by half-face application, the composition of the invention being applied to one half of the face, while one of the comparative examples was applied to the other half of the face.

| Composition | Example 1 according to the invention | Comparative Example 1 | Comparative Example 2 |
|---|---|---|---|
| Phase A1 | | | |
| Methyl glucose sesquistearate (Glucate SS) | 2% | 2% | 2% |
| Stearyl alcohol/ceteareth-20 | 2% | 2% | 2% |
| Preserving agents | 0.1% | 0.1% | 0.1% |
| 2-Octyldodecanol | 4% | 4% | 4% |
| Phase A2 | | | |
| Cyclopentasiloxane | 5% | 5% | 5% |
| Phase B1 | | | |
| Glycerol | 3% | 3% | 3% |
| Sodium magnesium silicate (clay) (platelets) | 0.5% | — | 0.5% |
| Demineralized water | qs 100% | qs 100% | qs 100% |
| Preserving agents | 0.25% | 0.25% | 0.25% |
| Phase B2 | | | |
| PEG-20 methyl glucose sesquistearate (Glucamate SSE 20) | 3% | 3% | 3% |
| Demineralized water | 19% | 19% | 19% |
| Phase C | | | |
| Nylon-12 (Orgasol) (spherical particles) | 2% | 2% | — |
| Polyamide fibers (Nylon-6,6) (Polyamide 0.9 Dtex, 0.3 mm—Paul Bonte Company) | 10% | 10% | 10% |
| Phase D | | | |
| Ammonium polyacryloyl-dimethyltaurate (Hostacerin AMPS from Clariant) | 0.2% | 0.2% | 0.2% |
| Quality of the composition obtained | creamy, fine and soft easy to apply | fluid, slides over the fingers | creamy and fine. Compared with |

-continued

| Composition | Example 1 according to the invention | Comparative Example 1 | Comparative Example 2 |
|---|---|---|---|
| | uniform deposit | pilling of the composition on application | Ex. 1: fibers more persistent on the skin, more difficult to apply, less uniform deposit |

Procedure: Phases A1 and A2 are heated separately (about 70° C.) with stirring and then mixed together. Similarly, phases B1 and B2 are heated separately (about 70° C.) with stirring and then mixed together. The mixture of B1 and B2 is then poured into the mixture of A1 and A2 with stirring. Phase D is then added and the resulting mixture is homogenized.

The three compositions have a white fibrous texture. The test demonstrates the advantage of the composition according to the invention, which does not pill when applied to the skin and gives a more uniform and easier deposit than the compositions of the comparative examples.

French Patent Application 0103767 filed Mar. 20, 2001 is incorporated herein by reference, as are all documents, publications, articles, standards, and patents referred to above.

Whenever a number range is disclosed all values and sub-ranges between stated values are included as if specifically written out.

The use of the invention composition is within the skill of the ordinary artisan in view of this disclosure, and depends in part on its ingredients and the desired effect. For example, a user can apply 0.1-5 g of composition to keratin material such as skin once or more daily, optionally over a long term.

Obviously, numerous modifications and variations of the present invention are possible in light of the above teachings. It is therefore to be understood that within the scope of the appended claims, the invention may be practiced otherwise than as specifically described herein.

The invention claimed is:

1. A composition comprising an oily phase dispersed in an aqueous phase, polyamide fibers, spherical polyamide particles, platelets selected from the group consisting of clays, talcs, micas, and mixtures thereof, and a nonionic surfactant emulsifier selected from the group consisting of a fatty acid ester of glucose which is optionally oxyalkylenated, a fatty acid ester of alkylglucose which is optionally oxyalkylenated, and mixtures thereof, wherein
the fibers have a length (L) ranging from 1 μm to 10 mm,
the fibers have a cross section that is within a circle of diameter (D) ranging from 1 nm to 100 μm,
the fibers have a shape factor (L/D) ranging from 5 to 150,
the fibers have a yarn count ranging from 0.15 to 30 denier,
the fibers are present in an amount ranging from 1% to 20% by weight relative to the total weight of the composition,
the spherical particles have a particle size ranging from 0.1 μm to 250 μm,
the spherical particles are present in an amount ranging from 0.5% to 25% by weight relative to the total weight of the composition,
the platelets have a length ranging from 0.01 to 100 μm, a width of from 0.01 to 100 μm and a height ranging from 0.1 to 1,000 nm,
the platelets are present in an amount ranging from 0.25% to 25% by weight relative to the total weight of the composition,
the oily phase represents from 15% to 30% by weight relative to the total weight of the composition, and
the composition is an oil-in-water emulsion.

2. The composition according to claim 1, wherein the fibers have a length (L) ranging from 0.1 mm to 1.5 mm.

3. The composition according to claim 1, wherein the fibers have a cross section that is within a circle of diameter (D) ranging from 1 nm to 50 μm.

4. The composition according to claim 1, wherein the fibers have a yarn count ranging from 0.18 to 18 denier.

5. The composition according to claim 1, wherein said fibers are coated, functionalized, or coated and functionalized.

6. The composition according to claim 1, wherein the fibers are present in an amount ranging from 2% to 15% by weight relative to the total weight of the composition.

7. The composition according to claim 1, wherein the spherical particles have a particle size ranging from 1 μm to 150 μm.

8. The composition according to claim 1, wherein the spherical particles are present in an amount ranging from 1% to 10% by weight relative to the total weight of the composition.

9. The composition according to claim 1, wherein the platelets have a length ranging from 0.01 to 50 μm, a width of from 0.01 to 50 μm and a height ranging from 1 to 600 nm.

10. The composition according to claim 1, wherein the platelets are selected from the group consisting of clays, talcs, and mixtures thereof.

11. The composition according to claim 1, wherein the platelets are present in an amount ranging from 0.5% to 10% by weight relative to the total weight of the composition.

12. The composition according to claim 1, wherein the amount of emulsifier ranges from 0.1% to 15% by weight relative to the total weight of the composition.

13. The composition according to claim 1, wherein said composition is a cosmetic composition.

14. A process for treating the skin, the hair, the eyelashes and/or the lips, comprising applying the composition of claim 13 to the skin, the hair, the eyelashes, and/or the lips.

15. The composition according to claim 1, further comprising a physiologically acceptable medium.

16. A process for treating the skin, the hair, the eyelashes and/or the lips, comprising applying the composition of claim 15 to the skin, the hair, the eyelashes, and/or the lips.

17. The composition according to claim 1, wherein the composition comprises a nonionic surfactant emulsifier which is a fatty acid ester of glucose, optionally oxyalkylenated.

18. The composition according to claim 1, wherein the composition comprises a nonionic surfactant emulsifier which is a fatty acid ester of alkylglucose, optionally oxyalkylenated.

19. The composition according to claim 1, wherein the composition comprises a nonionic surfactant emulsifier which is an oxyalkylenated fatty acid ester of glucose or of alkylglucose.

20. The composition according to claim 1, wherein the platelets are selected from the group consisting of talcs, micas, and mixtures thereof.

21. The composition according to claim 1, wherein the platelets are selected from the group consisting of clays, micas, and mixtures thereof.

* * * * *